(12) United States Patent
Demaine et al.

(10) Patent No.: US 7,288,564 B2
(45) Date of Patent: Oct. 30, 2007

(54) INDOLE DERIVATIVES

(75) Inventors: Derek Anthony Demaine, Stevenage (GB); Gerard Martin Paul Giblin, The Frythe (GB); Rachel Elizabeth Hosking, Stevenage (GB); Graham George Adam Inglis, Stevenage (GB); Xiao Qing Lewell, Stevenage (GB); Simon John Fawcett MacDonald, Stevenage (GB); Andrew McMurtrie Mason, Stevenage (GB); Martin Edward Swarbrick, Stevenage (GB)

(73) Assignee: Glaxo Group Limited, Middlesex (GB)

( * ) Notice: Subject to any disclaimer, the term of this patent is extended or adjusted under 35 U.S.C. 154(b) by 412 days.

(21) Appl. No.: 10/450,894

(22) PCT Filed: Dec. 20, 2001

(86) PCT No.: PCT/GB01/05701

§ 371 (c)(1),
(2), (4) Date: Dec. 10, 2003

(87) PCT Pub. No.: WO02/50031

PCT Pub. Date: Jun. 27, 2002

(65) Prior Publication Data

US 2004/0092569 A1  May 13, 2004

(30) Foreign Application Priority Data

Dec. 21, 2000  (GB) .................... 0031315.5

(51) Int. Cl.
*A61K 31/404* (2006.01)
*C07D 209/04* (2006.01)

(52) U.S. Cl. ............... 514/419; 548/490; 548/491; 514/415

(58) Field of Classification Search ........... 548/490, 548/491; 514/415, 419
See application file for complete search history.

(56) References Cited

U.S. PATENT DOCUMENTS 4,251,446 A * 2/1981 Crounse et al. ............. 548/525
4,322,352 A * 3/1982 Crounse et al. ............. 548/456
5,075,313 A * 12/1991 Yu et al. ................... 514/266.2
5,559,125 A * 9/1996 Kulagowski et al. ....... 514/312
6,833,387 B1 * 12/2004 Faull et al. ................. 514/484

FOREIGN PATENT DOCUMENTS

WO  WO 00/18744  4/2000
WO  WO 00/21532  4/2000

OTHER PUBLICATIONS

Yu et al (1992): STN International HCAPLUS database, Columbus (OH), accession No. 1992: 128964.*
Edwards et al (1950): STN International HCAPLUS database, Columbus (OH), accession No. 1950: 734.*

* cited by examiner

*Primary Examiner*—Golam M. M. Shameem
(74) *Attorney, Agent, or Firm*—Grace C. Hsu; Mary E. McCarthy; Charles M. Kinzig

(57) ABSTRACT

Compounds of formula (I)

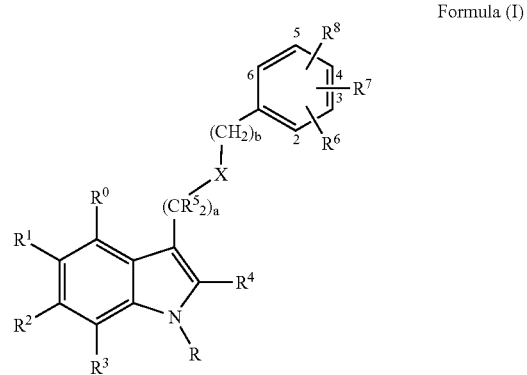

Formula (I)

or salts or solvates thereof or physiologically functional derivatives thereof are potent binders at the EP4 receptor and are of use in the treatment or prevention of conditions such as a pain, inflammatory, immunological, bone, neurodegenerative or renal disorder.

8 Claims, No Drawings

INDOLE DERIVATIVES

CROSS REFERENCES TO RELATED APPLICATIONS

This application is a National Stage Application filed under 35 U.S.C. §371 of PCT/GB01/05701, filed on Dec. 20, 2001, which claims priority of GB Application No. GB0031315.5, filed Dec. 20, 2000.

This invention relates to indole derivatives, to processes for their preparation, to pharmaceutical compositions containing them and to their use in medicine.

The EP4 receptor is a 7-transmembrane receptor and its natural ligand is the prostaglandin $PGE_2$. $PGE_2$ also has affinity for the other EP receptors (types EP1, EP2 and EP3). The EP4 receptor is associated with smooth muscle relaxation, inflammation, lymphocyte differentiation, bone metabolism processes, allergic activities, promotion of sleep, renal regulation and gastric or enteric mucus secretion. We have now found a novel group of compounds which bind with high affinity to the EP4 receptor.

The invention thus provides compounds of formula (I)

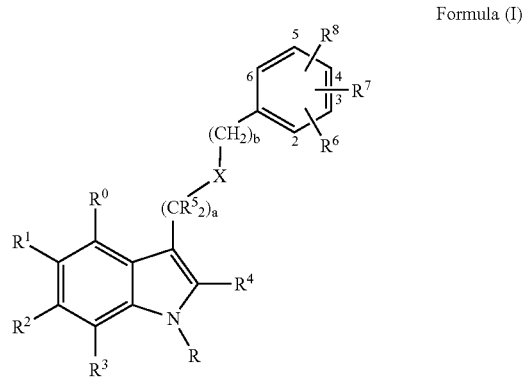

Formula (I)

or salts or solvates thereof or physiologically functional derivatives thereof in which:

a=0, 1 or 2;

b=0 or 1;

X is C(O)NR or NRC(O);

R is H or $C_{1-4}$alkyl;

$R^0$, $R^1$, $R^2$ and $R^3$ are each independently selected from H, halogen, $C_{1-6}$alkyl, $SC_{1-6}$-alkyl, $C_{1-6}$alkoxy, $OCF_3$, $OCH_2CF_3$, O-cyclopropyl, $OCH_2$-cyclopropyl, $NH_2$, $NHC_{1-6}$alkyl, $N(C_{1-6}alkyl)_2$, $NO_2$, OH, $CH_2OC_{1-6}$alkyl, $CH_2OH$, aryl$C_{1-6}$alkylenoxy, $C_{1-6}$alkyl-$SO_2NH$—$C_{1-4}$alkylene, aryl or heteroaryl;

$R^4$ is selected from H, $C_{1-6}$alkyl, aryl or heteroaryl;

each $R^5$ is independently selected from H, $CH_3$ or F;

$R^6$ is selected from $SO_3H$, $SO_2NH_2$, $CH_2CO_2H$, $SO_2NHCOR$, $CONHSO_2R$, $P(O)(OH)_2$, heteroaryl or C(O)Z where Z is OH or $NR^9{}_2$ where each $R^9$ is independently selected from H, $C_{1-6}$alkyl or $SO_2(CH_2)_c$aryl where c is 0 or 1;

$R^7$ is selected from H, $C_{1-6}$alkyl, $C_{1-6}$-alkoxy, halogen, $NO_2$, $CH=CHCO_2C_{1-6}$-alkyl, $NHCOC_{1-6}$alkyl, $C_{1-2}$perfluoroalkyl, OH or $CO_2R^{10}$ where $R^{10}$ is selected from H or $C_{1-6}$alkyl; and $R^8$ is H, or, when $R^7$ is $C_{1-6}$alkyl, $C_{1-6}$-alkoxy or halogen, $R^8$ may also be $C_{1-6}$alkyl, $C_{1-6}$alkoxy or halogen; or $R^7$, $R^8$ and the benzene ring to which they are attached are taken together to form a napthyl group or a benzene ring fused to a heteroaryl group; or $R^7$ and $R^8$ are taken together to form a vicinal $OC(CH_3)_2O$ group.

As used herein, the term "solvate" refers to a complex of variable stoichiometry formed by a solute (in this invention, a compound of formula (I) or a salt thereof or a physiologically functional derivative thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

As used herein, the term "physiologically functional derivative" refers to any pharmaceutically acceptable derivative of a compound of the present invention, for example, an ester or an amide, which upon administration to a mammal, such as a human, is capable of providing (directly or indirectly) a compound of formula (I) or an active metabolite or residue thereof. It will be appreciated by those skilled in the art that the compounds of formula (I) may be modified to provide physiologically functional derivatives thereof at any of the functional groups in the compounds, and that the compounds of formula (I) may be so modified at more than one position.

It will be appreciated that, for pharmaceutical use, the "salt or solvate" referred to above will be a pharmaceutically acceptable salt or solvate. However, other salts or solvates may find use, for example, in the preparation of a compound of formula (I) or in the preparation of a pharmaceutically acceptable salt or solvate thereof.

Pharmaceutically acceptable salts include those described by Berge, Bighley and Monkhouse, *J. Pharm. Sci.*, 1977, 66, 1-19. Suitable pharmaceutically acceptable salts include acid addition salts formed from the addition of inorganic acids or organic acids, preferably inorganic acids. Examples of suitable acid addition salts include hydrochlorides, hydrobromides, sulphates and acetates. Further representative examples of pharmaceutically acceptable salts include those formed from maleic, fumaric, benzoic, ascorbic, pamoic, succinic, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitirc acids. Suitable pharmaceutically acceptable salts also include alkali metal salts formed from the addition of alkali metal bases such as alkali metal hydroxides. An example of a suitable alkali metal salt is a sodium salt.

As used herein, the terms "alkyl" and "alkylene" (when used as a group or as part of a group) refer to a straight or branched hydrocarbon chain containing the specified number of carbon atoms. For example, $C_{1-6}$alkyl means a straight or branched hydrocarbon chain containing at least 1 and at most 6 carbon atoms. Examples of alkyl as used herein include, but are not limited to; methyl, ethyl, n-propyl, i-propyl, n-butyl, s-butyl and t-butyl. Examples of alkylene as used herein include, but are not limited to, methylene, ethylene, propylene and butylene.

As used herein, the term "perfluoroalkyl" (when used as a group or as part of a group) refers to a straight or branch d hydrocarbon chain containing the specified number of carbon atoms wherein every hydrogen atom is substituted by a fluorine atom. For example, $C_{1-2}$perfluoroalkyl means a hydrocarbon chain containing at least 1 and at most 2 carbon atoms wherein every hydrogen atom is substituted by a fluorine atom. Examples of perfluoroalkyl as used herein include trifluoromethyl and pentafluoroethyl.

As used herein, the terms "alkoxy" and "alkylenoxy" (when used as a group or as part of a group) refers to a straight or branched hydrocarbon chain containing the specified number of carbon atoms and having an oxygen atom attached to the chain. For example, $C_{1-6}$alkoxy means a straight or branched alkyl chain containing at least 1 and at most 6 carbon atoms and having an oxygen atom attached to the chain. Examples of alkoxy as used herein include, but are not limited to; methoxy, ethoxy, n-propoxy, i-propoxy, n-butoxy, s-butoxy and t-butoxy. Examples of alkylenoxy as used herein include, but are not limited to; methylenoxy, ethylenoxy and propylenoxy.

As used herein, the term "aryl" (when used as a group or as part of a group) refers to a phenyl or naphthyl group. Said aryl groups may be optionally substituted with one or more groups selected from $C_{1-6}$alkyl, $C_{1-6}$alkoxy, $NO_2$, hydroxy$C_{1-4}$alkylene, $CONH_2$, $CONH(C_{1-6}$alkyl), $CON(C_{1-6}$alkyl$)_2$, halogen or phenyl. Where the aryl group is a phenyl group it may also be substituted so as to provide a methylenedioxyphenyl group.

As used herein, the term "heteroaryl" refers to a monocyclic five to seven membered aromatic ring. These heteroaryl rings contain one or more nitrogen, sulfur, or oxygen heteroatoms, where N-oxides, sulfur oxides and sulfur dioxides are permissible heteroatom substitutions. Examples of heteroaryl include furan, thiophene, pyrrole, imidazole, pyrazole, triazole, tetrazole, thiazole, oxazole, isoxazole, oxadiazole, thiadiazole, isothiazole, pyridine, pyridazine, pyrazine and pyrimidine. Said heteroaryl groups may be optionally substituted with with one or more $C_{1-6}$alkyl groups.

As used herein, the terms "halogen" or "halo" refer to fluorine, chlorine, bromine and iodine.

As used herein, the term "vicinal" when applied to a diradical group means that the free radical ends of the group are attached to adjacent carbon atoms on another group. Thus a "vicinal $OC(CH_3)_2O$ group" attached to a phenyl group provides a group having the formula:

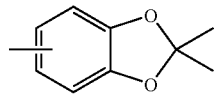

Certain compounds of formula (I) and certain salts or solvates or physiologically functional derivatives thereof may exist in stereoisomeric forms (e.g. they may contain one or more asymmetric carbon atoms or they may exhibit cis-trans isomerism). Each of the individual stereoisomers (including enantiomers and diastereomers) and all possible mixtures of these (including racemic mixtures) are included within the scope of the present invention. Likewise, it is understood that certain compounds of formula (I) and certain salts or solvates or physiologically functional derivatives thereof may exist in tautomeric forms other than that shown in the formula and these are also included within the scope of the present invention.

In another aspect of the present invention, a is 1.
In another aspect of the present invention, b is 0.
In another aspect of the present invention X is C(O)NR.
In another aspect of the present invention, R is H or $CH_3$. Preferably R is H.

In another aspect of the present invention, $R^0$ is H, except when $R^1$ is H, in which case $R^0$ may be hydrogen or chlorine.

In another aspect of the present invention, $R^1$ is H.

In another aspect of the present invention, $R^1$ is $C_{1-6}$alkoxy. Preferably $R^1$ is methoxy.

In another aspect of the present invention, $R^1$ is aryl$C_{1-6}$alkylenoxy. Preferably $R^1$ is phenyl$C_{1-6}$alkylenoxy, more preferably $PhCH_2O$.

In another aspect of the present invention, $R^1$ is halogen. Preferably $R^1$ is fluorine, chlorine or bromine.

In another aspect of the present invention, $R^1$ is aryl. Preferably $R^1$ is phenyl substituted with one substituent selected from $C_{1-6}$alkoxy (preferably methoxy), $NO_2$ or halogen (preferably fluorine); or phenyl substituted so as to provide a 1,2-methylenedioxyphenyl group. In particular, $R^1$ may be selected from:

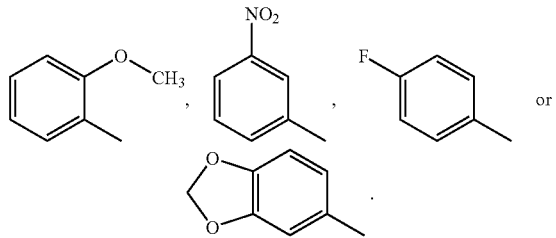

In another aspect of the present invention, $R^1$ is heteroaryl. Preferably $R^1$ is thiophene or isoxazole optionally substituted with one or two $C_{1-6}$alkyl (preferably methyl) groups. In particular, $R^1$ may be selected from:

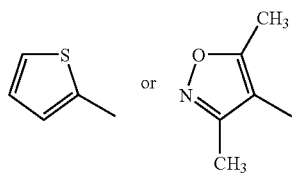

In another aspect of the present invention, $R^2$ is H, except when $R^1$ is methoxy, in which case $R^2$ is selected from H or methoxy. In another aspect of the present invention, $R^3$ is H, except when $R^1$ is H, in which case $R^3$ is selected from H or phenyl$C_{1-6}$alkylenoxy (preferably $PhCH_2O$).

In another aspect of the present invention, $R^4$ is H.
In another aspect of the present invention, $R^4$ is $CH_3$.
In another aspect of the present invention, $R^4$ is phenyl or phenyl substituted by a fluorine atom (preferably in the para position).

In another aspect of the present invention, each $R^5$ is H.
In another aspect of the present invention, $R^6$ is $CO_2H$.
In another aspect of the present invention, $R^6$ is tetrazole.
In another aspect of the present invention, $R^6$ is in the 2-position of the phenyl ring as those positions are numbered in formula (I) above.

In another aspect of the present invention, $R^7$ is H.
In another aspect of the present invention, $R^7$ is $C_{1-6}$alkyl. Preferably $R^7$ is methyl or ethyl, most preferably methyl. When $R^7$ is $C_{1-6}$alkyl it is preferably in the 4- or 5-position of the phenyl ring as those positions are numbered in formula (I) above. When $R^7$ is $C_{1-6}$alkyl it is most preferably in the 5-position of the phenyl ring as those positions are numbered in formula (I) above. Thus, in a particular aspect, $R^7$ is methyl in the 5-position of the phenyl ring as those positions are numbered in formula (I) above.

In another aspect of the present invention, $R^7$ is halogen. Preferably $R^7$ is fluorine, chlorine or bromine. When $R^7$ is halogen it is preferably in the 4-, 5- or 6-position of the phenyl ring as those positions are numbered in formula (I) above.

In another aspect of the present invention, $R^7$ is $NO_2$. When $R^7$ is $NO_2$ it is preferably in the 5-position of the phenyl ring as those positions are numbered in formula (I) above.

In another aspect of the present invention, $R^7$ is $CH=CHCO_2C_{1-6}$alkyl. Preferably $R^7$ is $CH=CHCO_2{}^tBu$. When $R^7$ is $CH=CHCO_2C_{1-6}$alkyl it is preferably in the 4-position of the phenyl ring as those positions are numbered in formula (I) above.

In another aspect of the present invention, $R^7$ is $C_{1-2}$perfluoroalkyl. Preferably $R^7$ is trifluoromethyl. When $R^7$ is $C_{1-2}$perfluoroalkyl it is preferably in the 5-position of the phenyl ring as those positions are numbered in formula (I) above.

In another aspect of the present invention, $R^7$ is OH. When $R^7$ is OH it is preferably in the 6-position of the phenyl ring as those positions are numbered in formula (I) above.

In another aspect of the present invention, $R^8$ is H, except when $R^7$ halogen, in which case $R^8$ is selected from H or halogen. When $R^8$ is halogen it is preferably in the 4-, 5- or 6-position of the phenyl ring as those positions are numbered in formula (I) above (and depending upon the position of $R^7$).

It is to be understood that the present invention covers all combinations of particular aspects of the invention as described hereinabove. In particular, the present invention covers the following combinations of particular aspects of the invention.

In another aspect of the present invention, there are provided compounds of formula (I) above or salts or solvates thereof or physiologically functional derivatives thereof in which:
a=1;
b=0;
X=CONR;
R is H;
$R^0$ is H;
$R^1$ is H;
$R^2$ is H;
$R^3$ is H;
$R^4$ is selected from H, Me or Ph;
$R^5$ is H;
$R^6$ is $CO_2H$ in the 2-position of the phenyl ring as those positions are numbered in formula (I) above;
$R^7$ is in the 4-, 5- or 6-position of the phenyl ring as those positions are numbered in formula (I) above and is selected from H, $C_{1-6}$alkyl, halogen, $NO_2$, $CH=CHCO_2C_{1-6}$alkyl, $C_{1-2}$perfluoroalkyl or OH; and
$R^8$ is H, except when $R^7$ is halogen, in which case $R^8$ is in the 4-, 5- or 6-position of the phenyl ring as those positions are numbered in formula (I) above and is selected from H or halogen.

In another aspect of the present invention, there are provided compounds of formula (I) above or salts or solvates thereof or physiologically functional derivatives thereof in which:
a=1;
b=0;
X=CONR;
R is H;
$R^0$ is H;
$R^1$ is $C_{1-6}$alkoxy;
$R^2$ is selected from H or $C_{1-6}$alkoxy;
$R^3$ is H;
$R^4$ is selected from H, Me or Ph (which may be substituted by a halogen);
$R^5$ is H;
$R^6$ is in the 2-position of the phenyl ring as those positions are numbered in formula (I) above and is selected from tetrazole or $CO_2H$;
$R^7$ is in the 4-, 5- or 6-position of the phenyl ring as those positions are numbered in formula (I) above and is selected from H, $C_{1-6}$alkyl, halogen, $NO_2$, $CH=CHCO_2C_{1-6}$alkyl, $C_{1-2}$perfluoroalkyl or OH; and
$R^8$ is H, except when $R^7$ is halogen, in which case $R^8$ is in the 4-, 5- or 6-position of the phenyl ring as those positions are numbered in formula (I) above and is selected from H or halogen.

In another aspect of the present invention, there are provided compounds of formula (I) above or salts or solvates thereof or physiologically functional derivatives thereof in which:
a=1;
b=0;
X=CONR;
R is H;
$R^0$ is H;
$R^1$ is $C_{1-6}$alkoxy;
$R^2$ is selected from H or $C_{1-6}$alkoxy;
$R^3$ is H;
$R^4$ is selected from H or Me;
$R^5$ is H;
$R^6$ is $CO_2H$ in the 2-position of the phenyl ring as those positions are numbered in formula (I) above;
$R^7$ is in the 4- or 5-position of the phenyl ring as those positions are numbered in formula (I) above and is selected from H, $C_{1-6}$alkyl, $C_{1-2}$perfluoroalkyl, halogen or $NO_2$; and
$R^8$ is H.

In another aspect of the present invention, there are provided compounds of formula (I) above or salts or solvates thereof or physiologically functional derivatives thereof in which:
a=1;
b=0;
X=CONR;
R is H;
0 is H;
$R^1$ is halogen;
$R^2$ is H;
$R^3$ is H;
$R^4$ is selected from H or Me;
$R^5$ is H;
$R^6$ is $CO_2H$ in the 2-position of the phenyl ring as those positions are numbered in formula (I) above;
$R^7$ is in the 4-, 5- or 6-position of the phenyl ring as those positions are numbered in formula (I) above and is selected from H, $C_{1-6}$alkyl, halogen, $NO_2$, $CH=CHCO_2C_{1-6}$alkyl, $C_{1-2}$perfluoroalkyl or OH; and
$R^8$ is H, except when $R^7$ is halogen, in which case $R^8$ is in the 4-, 5- or 6-position of the phenyl ring as those positions are numbered in formula (I) above and is selected from H or halogen.

In another aspect of the present invention, there are provided compounds of formula (I) above or salts or solvates thereof or physiologically functional derivatives thereof in which:

a=1;
b=0;
X=CONR;
R is H;
$R^0$ is H;
$R^1$ is aryl;
$R^2$ is H;
$R^3$ is H;
$R^4$ is selected from H or Me;
$R^5$ is H;
$R^6$ is $CO_2H$ in the 2-position of the phenyl ring as those positions are numbered in formula (I) above;
$R^7$ is in the 4-, 5- or 6-position of the phenyl ring as those positions are numbered in formula (I) above and is selected from H, $C_{1-6}$alkyl, halogen, $NO_2$, $CH=CHCO_2C_{1-6}$alkyl, $C_{1-2}$perfluoroalkyl or OH; and
$R^8$ is H, except when $R^7$ is halogen, in which case $R^8$ is in the 4-, 5- or 6-position of the phenyl ring as those positions are numbered in formula (I) above and is selected from H or halogen.

In another aspect of the present invention, there are provided compounds of formula (I) above or salts or solvates thereof or physiologically functional derivatives thereof in which:

a=1;
b=0;
X=CONR;
R is H;
$R^0$ is H;
$R^1$ is heteroaryl;
$R^2$ is H;
$R^3$ is H;
$R^4$ is selected from H or Me;
$R^5$ is H;
$R^6$ is $CO_2H$ in the 2-position of the phenyl ring as those positions are numbered in formula (I) above;
$R^7$ is in the 4-, 5- or 6-position of the phenyl ring as those positions are numbered in formula (I) above and is selected from H, $C_{1-6}$alkyl, halogen, $NO_2$, $CH=CHCO_2C_{1-6}$alkyl, $C_{1-2}$perfluoroalkyl or OH; and
$R^8$ is H, except when $R^7$ is halogen, in which case $R^8$ is in the 4-, 5- or 6-position of the phenyl ring as those positions are numbered in formula (I) above and is selected from H or halogen.

In one aspect the invention provides the following compounds or salts or solvates thereof or physiologically functional derivatives thereof:

2-{[(5-methoxy-2-methyl-1H-indol-3-yl)acetyl]amino}benzoic acid,
2-{[(5-methoxy-2-methyl-1H-indol-3-yl)acetyl]amino}4-methylbenzoic acid,
2-[(1H-indol-3-ylacetyl)amino]4-methylbenzoic acid,
4-methyl-2-{[(2-methyl-1H-indol-3-yl)acetyl]amino}benzoic acid,
2-{[(5-fluoro-1H-indol-3-yl)acetyl]amino}-4-methylbenzoic acid,
2-({[5-(benzyloxy)-1H-indol-3-yl]acetyl}amino)-4-methylbenzoic acid,
2-{[(5-bromo-1H-indol-3-yl)acetyl]amino}-4-methylbenzoic acid,
2-{[(5-methoxy-1H-indol-3-yl)acetyl]amino}-4-methylbenzoic acid,
4-bromo-2-{[(5-methoxy-2-methyl-1H-indol-3-yl)acetyl]amino}benzoic acid,
4-fluoro-2-{[(5-methoxy-2-methyl-1H-indol-3-yl)acetyl]amino}benzoic acid,
4-chloro-2-{[(5-methoxy-2-methyl-1H-indol-3-yl)acetyl]amino}benzoic acid,
2-{[(5-methoxy-2-methyl-1H-indol-3-yl)acetyl]amino}-4-nitrobenzoic acid,
4-[(1E)-3-tert-butoxy-3-oxoprop-1-enyl]-2-{[(5-methoxy-2-methyl-1H-indol-3-yl)acetyl]amino}benzoic acid,
5-chloro-2-{[(5-methoxy-2-methyl-1H-indol-3-yl)acetyl]amino}benzoic acid,
4,5-difluoro-2-{[(5-methoxy-2-methyl-1H-indol-3-yl)acetyl]amino}benzoic acid,
4-ethyl-2-{[(5-methoxy-2-methyl-1H-indol-3-yl)acetyl]amino}benzoic acid,
2-{[(5-methoxy-2-methyl-1H-indol-3-yl)acetyl]amino}-5-methylbenzoic acid,
2-{[(5-methoxy-2-methyl-1H-indol-3-yl)acetyl]amino}-4-(trifluoromethyl)benzoic acid,
3-hydroxy-2-{[(5-methoxy-2-methyl-1H-indol-3-yl)acetyl]amino}benzoic acid,
3,5-dichloro-2-{[(5-methoxy-2-methyl-1H-indol-3-yl)acetyl]amino}benzoic acid,
2-{[(5,6-dimethoxy-2-methyl-1H-indol-3-yl)acetyl]amino}-4-methylbenzoic acid,
2-{[(5-chloro-2-methyl-1H-indol-3-yl)acetyl]amino}-4-methylbenzoic acid,
2-({[7-(benzyloxy)-1H-indol-3-yl]acetyl}amino)-4-methylbenzoic acid,
2-{[(4-chloro-1H-indol-3-yl)acetyl]amino}-4-methylbenzoic acid,
4-methyl-2-{[(2-phenyl-1H-indol-3-yl)acetyl]amino}benzoic acid, and
2-{[(5,6-dimethoxy-2-methyl-1H-indol-3-yl)acetyl]amino}benzoic acid.

The compounds of the invention bind to the EP4 receptor and are therefore useful in treating EP4 receptor mediated diseases.

In view of their ability to bind to the EP4 receptor, the compounds of the invention are useful in the treatment of the disorders that follow. Thus, the compounds of formula (I) are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint strucure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; postherpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) are also useful in the treatment of immunological diseases such as autoimmune diseases, immunological deficiency diseases, diseases of abnormal platelet function (e.g. occlusive vascular diseases) or diseases associated with organ transplantation. The compounds of formula (I) are also effective in increasing the latency of HIV infection.

The compounds of formula (I) are also useful for the preparation of a drug with diuretic action.

The compounds of formula (I) are also useful in the treatment of impotence or erectile dysfunction.

The compounds of formula (I) are also useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and. bursitis. In a further aspect, compounds of formula (I) may be useful in inhibiting bone resorption and/or promoting bone generation.

The compounds of formula (I) are also useful for attenuating the hemodynamic side effects of NSAIDs and COX-2 inhibitors.

The compounds of formula (I) are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of formula (I) are also useful in the treatment of neurodegenerative diseases and neurodegeneration such as dementia, particularly degenerative dementia (including senile dementia, Alzheimer's disease, Pick's disease, Huntington's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) are also useful in the treatment of neuroprotection and in the treatment of neurodegeneration following stroke, cardiac arrest, pulmonary bypass, traumatic brain injury, spinal cord injury or the like.

The compounds of formula (I) are also useful in the treatment of tinnitus.

The compounds of formula (I) are also useful in preventing or reducing dependence on, or preventing or reducing tolerance or reverse tolerance to, a dependence—inducing agent. Examples of dependence inducing agents include opioids (e.g. morphine), CNS depressants (e.g. ethanol), psychostimulants (e.g. cocaine) and nicotine.

The compounds of formula (I) are also useful in the treatment of complications of Type 1 diabetes (e.g. diabetic microangiopathy, diabetic retinopathy, diabetic neohropathy, macular degeneration, glaucoma), nephrotic syndrome, aplastic anaemia, uveitis, Kawasaki disease and sarcoidosis.

The compounds of formula (I) are also useful in the treatment of kidney dysfunction (nephritis, particularly mesangial proliferative glomerulonephritis, nephritic syndrome), liver dysfunction (hepatitis, cyrrhosis), gastrointestinal dysfunction (diarrhoea) and colon cancer.

Certain of the compounds of the invention have been shown to be potent and selective EP4 receptor antagonists. Accordingly, in a further aspect of the invention, there is provided the use of compounds of formula (I) and pharmaceutically acceptable derivatives thereof in the treatment of disorders ameliorated by EP4 receptor antagonism.

It is to be understood that reference to treatment includes both treatment of established symptoms and prophylactic treatment, unless explicitly stated otherwise.

According to a further aspect of the invention, we provide a compound of formula (I) or a pharmaceutically acceptable derivative thereof for use in human or veterinary medecine.

According to another aspect of the invention, we provide a compound of formula (I) or a pharmaceutically acceptable derivative thereof for use in the treatment of a condition which is mediated by the action of $PGE_2$ at EP4 receptors.

According to another aspect of the invention, we provide a compound of formula (I) or a pharmaceutically acceptable derivative thereof for use in the treatment of a condition which is ameliorated by EP4 receptor antagonism.

According to a further aspect of the invention, we provide a method of treating a human or animal subject suffering from a condition which is mediated by the action of $PGE_2$ at EP4 receptors which comprises administering to said subject an effective amount of a compound of formula (I) or a pharmaceutically acceptable derivative thereof.

According to a further aspect of the invention, we provide a method of treating a human or animal subject suffering from a condition which is ameliorated by an EP4 receptor antagonist which comprises administering to said subject an effective amount of a compound of formula (I) or a pharmaceutically acceptable derivative thereof.

According to a further aspect of the invention we provide a method of treating a human or animal subject suffering from a pain, inflammatory, immunological, bone, neurodegenerative or renal disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by the action of $PGE_2$ at EP4 receptors.

According to another aspect of the invention, we provide the use of a compound of formula (I) or a pharmaceutically acceptable derivative thereof for the manufacture of a therapeutic agent for the treatment of a condition which is am liorated by EP4 receptor antagonism.

According to another aspect of the invention we provide the use of a compound of formula (I) or a pharmaceutically acceptable derivative thereof for the manufacture of a therapeutic agent for the treatment or prevention of a condition such as a pain, inflammatory, immunological, bone, neurodegenerative or renal disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, we provide a pharmaceutical composition comprising a compound of formula (I) or a pharmaceutically acceptable derivative thereof adapted for use in human or veterinary medicine.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The EP4 receptor compounds for use in the instant invention may be used in combination with other therapeutic agents, for example COX-2 inhibitors, such as celecoxib, rofecoxib, valdecoxib or parecoxib; 5-lipoxygenase inhibitors; NSAID's, such as diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with one or more further therapeutic agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of compounds of formula (I) or their pharmaceutically acceptable salts for the treatment of man is from 0.01 to 10 mg/kg body weight per day and more particularly 0.1 to 3 mg/kg body weight per day, which may be administered as a single or divided dose, for example one to four times per day. The dose range for adult human beings is generally from 8 to 1000 mg/day, such as from 20 to 800 mg/day, preferably 35 to 200 mg/day.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

Compounds of formula (I) and salts and solvates thereof and physiologically functional derivatives thereof may be prepared by any method known in the art for the preparation of compounds of analogous structure.

Compounds of formula (I) and salts and solvates thereof and physiologically functional derivatives thereof may be prepared by a process which comprises:

(A), coupling an acid of formula (II)

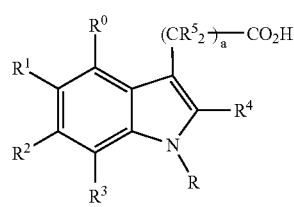

or a protected derivative thereof, with an amine of formula (III)

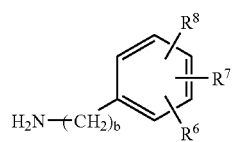

or a protected derivative thereof; or (B), coupling an acid of formula (V)

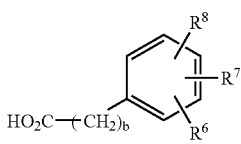

or a protected derivative thereof, with an amine of formula (IV)

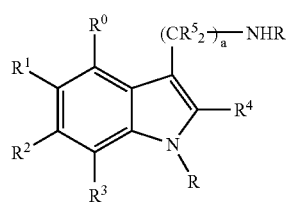

or a protected derivative thereof; or (C), interconversion of a compound of formula (I) into another compound of formula (I); or (D), deprotecting a protected derivative of compound of formula (I); and optionally converting compounds of formula (I) prepared by any one of the processes (A) to (D) into a salt or solvate thereof or a physiologically functional derivative thereof.

Suitable methods for the preparation of compounds of formula (I) and salts and solvates thereof and physiologically functional derivatives thereof are described below, and form a further aspect of the invention. In the Schemes that follow R to $R^8$, a, b and X are as defined in formula (I) above unless otherwise stated; CDI is 1,1'-carbonyldiimidazole, THF is tetrahydrofuran and DCM is dichloromethane.

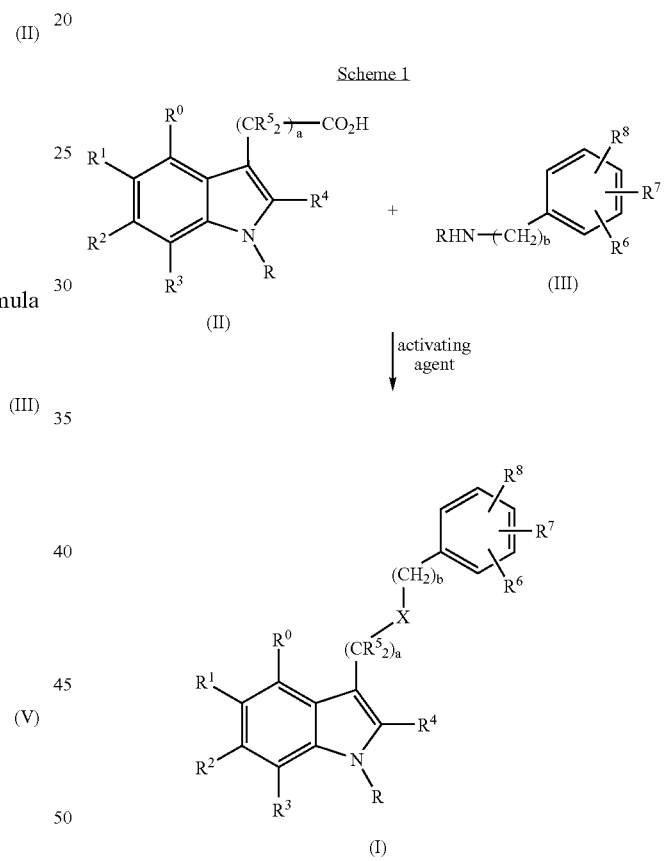

Scheme 1

Referring to Scheme 1 above, compounds of formula (I) wherein X is C(O)NR may be prepared by coupling a compound of formula (II) with a compound of formula (III) in the presence of an activating agent, such as CDI, in a suitable aprotic solvent, such as THF or CDM. Such couplings are described in many organic texts such as 'Principles of Peptide Synthesis' by Miklos Bodanszky (Springer Verlag, 1984) chapter 2, incorporated herein by reference.

As shown in Scheme 2 below, compounds of formula (I) wherein X is NRC(O) may be prepared by coupling a compound of formula (IV) with a compound of formula (V) in an analogous manner to Scheme 1.

Scheme 2

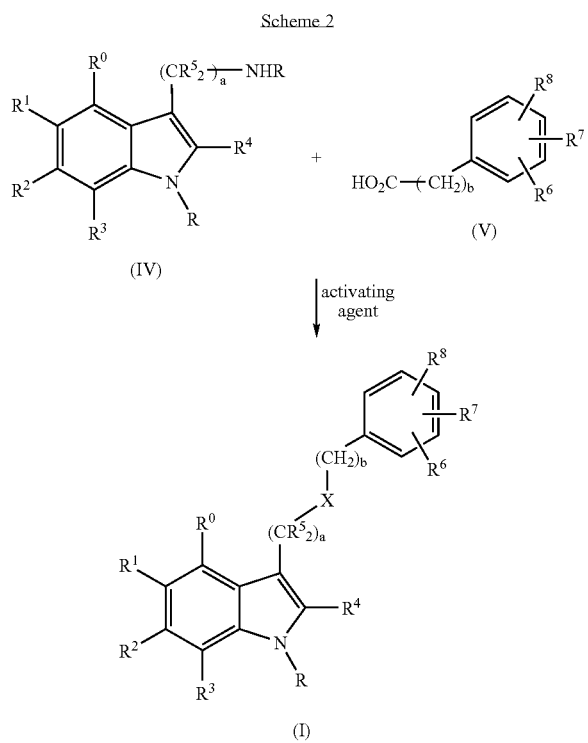

Compounds of formulae (II) and (IV) are either known compounds or may be prepared by literature methods such as the Fischer Indole synthesis described in 'Advanced Organic Chemistry' by Jerry March, fourth edition (John Wiley & Sons, 1992) page 1141, incorporated herein by reference.

Compounds of formulae (III) and (V) are either known compounds or may be prepared by well known literature methods.

It will be appreciated by those persons skilled in the art that compounds of formulae (I) to (V) may be prepared by interconversion, utilising other compounds of formulae (I) to (V) as precursors.

As will be appreciated by those skilled in the art it may be necessary or desirable at any stage in the synthesis of any of the compounds of formulae (I) to (V) to protect one or more sensitive groups in the molecule so as to prevent undesirable side reactions. The protecting groups used in the preparation of compounds of formulae (I) to (V) may be used in conventional manner. See, for example, those described in 'Protective Groups in Organic Synthesis' by Theodora W Green and Peter G M Wuts, second edition (John Wiley and Sons, 1991), incorporated herein by reference, which also describes methods for the removal of such groups.

Solvates (e.g. hydrates) or salts of a compound of the invention may be formed during the work-up procedure of any one of the aforementioned process steps.

The examples that follow illustrate the invention but do not limit the invention in any way. All temperatures are in ° C. Liquid chromatography/mass spectrometry (LC/MS) was performed using a 3.3 cm×4.6 mm ID, 3 μm ABZ+PLUS column at a flow rate of 3 ml/min and with an injection volume of 5 μl at room temperature. The solvents used were 0.1% formic acid +99.9% 10 mM ammonium acetate (solvent A) and 95% acetonitrile+4.95% water+0.05% formic acid (solvent B). The solvent gradient used is given in the table below. The mass spectrometer was a Micromass series II MS HP1050.

| Time | A % | B % |
|------|-----|-----|
| 0.00 | 100 | 0 |
| 0.70 | 100 | 0 |
| 4.20 | 0 | 100 |
| 5.30 | 0 | 100 |
| 5.50 | 100 | 0 |

EXAMPLE 1

2-{[(5-methoxy-2-methyl-1H-indol-3-yl)acetyl]amino}-4-methylbenzoic acid

5-Methoxy-2-methyl-3-indol acetic acid (1.32 g, obtainable from Aldrich Chemical Co), carbonyldiimidazole (1.07 g) and tetrahydrofuran (27 ml) were stirred under nitrogen at room temperature for 30 min. Methyl 4-methylanthranilate (1.00 g) and pyridinium tosylate (3.62 g) were added and the mixture refluxed for 24 h. After cooling, the solvent was removed in vacuo and the residue diluted with dichloromethane (200 ml) and washed with 2M hydrochloric acid (50 ml), 2M sodium hydroxide (50 ml), water (50 ml), brine (40 ml) and dried ($MgSO_4$). Solvent removal in vacuo afforded methyl 2-{[(5-methoxy-2-methyl-1H-indol-3-yl)acetyl]amino}-4-methylbenzoate (2.09 g). LC/MS: $T_R$ 3.52 min, $MH^+$ 367.

Methyl 2-{[(5-methoxy-2-methyl-1H-indol-3-yl)acetyl]amino}4-methylbenzoate 0.916 g), lithium hydroxide (0.600 g), water (50 ml) and tetrahydrofuran (50 ml) were refluxed for 3 h. After cooling, the tetrahydrofuran was removed in vacuo the aqueous residue washed with ether (2×25 ml) and then acidified with glacial acetic acid (1.6 ml). The precipitated solid was filtered off, washed with water and dried in vacuo to afford the title compound (0.757 g). LC/MS $T_R$ 3.58 min, $MH^+$ 353.

The following compounds were prepared in an analogous manner to Example 1:

| Example No. | Compound Name | $MH^+$ | $MH^-$ | $T_R$ (min) |
|---|---|---|---|---|
| 2 | 2-[(1H-indol-3-ylacetyl)amino]-4-methylbenzoic acid | 309 | 307 | 3.70 |
| 3 | 4-methyl-2-{[(2-methyl-1H-indol-3-yl)acetyl]amino}benzoic acid | 323 | 321 | 3.73 |
| 4 | 2-{[(5-fluoro-1H-indol-3-yl)acetyl]amino}-4-methylbenzoic acid | | 325 | 3.81 |
| 5 | 2-({[5-(benzyloxy)-1H-indol-3-yl]acetyl}amino)-4-methylbenzoic acid | 415 | 413 | 4.10 |
| 6 | 2-{[(5-bromo-1H-indol-3-yl)acetyl]amino}-4-methylbenzoic acid | | 385, 387 | 4.25 |
| 7 | 2-{[(5-methoxy-1H-indol-3-yl)acetyl]amino}-4-methylbenzoic acid | 339 | 337 | 3.54 |
| 8 | 4-bromo-2-{[(5-methoxy-2-methyl-1H-indol-3-yl)acetyl]amino}benzoic acid | 417, 419 | | 4.36 |

EXAMPLE 9

4-methyl-2-{[(2-phenyl-1H-indol-3-yl)acetyl]amino}benzoic acid

2-Phenyl-3-indole acetic acid (0.166 g), 1-(3-dimethylaminopropyl)-3-ethylcarbodiimide hydrochloride (0.127 g) and 4-methylanthranilic acid (0.100 g) in dichloromethane (20 ml) were refluxed for 48 h under nitrogen. The solvent was then removed and the residue purified using mass spectroscopy directed automated HPLC to afford the title compound (0.053 g). LC/MS $T_R$ 3.58 min, MH$^+$ 384.

The following compounds were prepared in an analogous manner to Example 9:

| Example No. | Compound Name | MH$^+$ | MH$^-$ | $T_R$ (min) |
|---|---|---|---|---|
| 10 | 4-fluoro-2-{[(5-methoxy-2-methyl-1H-indol-3-yl)acetyl]amino}benzoic acid | 357 | 355 | 3.76 |
| 11 | 4-chloro-2-{[(5-methoxy-2-methyl-1H-indol-3-yl)acetyl]amino}benzoic acid | 373, 375 | 371, 373 | 4.20 |
| 12 | 2-{[(5-methoxy-2-methyl-1H-indol-3-yl)acetyl]amino}-4-nitrobenzoic acid | 384 | 382 | 4.27 |
| 13 | 2-{[(5-methoxy-2-methyl-1H-indol-3-yl)acetyl]amino}benzoic acid | 339 | | |
| 14 | 5-chloro-2-{[(5-methoxy-2-methyl-1H-indol-3-yl)acetyl]amino}benzoic acid | 373, 375 | | 4.20 |
| 15 | 4,5-difluoro-2-{[(5-methoxy-2-methyl-1H-indol-3-yl)acetyl]amino}benzoic acid | 375 | | 4.24 |
| 16 | 2-{[(5-methoxy-2-methyl-1H-indol-3-yl)acetyl]amino}-5-methylbenzoic acid | 353 | | 3.48 |
| 17 | 2-{[(5-methoxy-2-methyl-1H-indol-3-yl)acetyl]amino}-4-(trifluoromethyl)benzoic acid | 407 | | 4.43 |
| 18 | 3-hydroxy-2-{[(5-methoxy-2-methyl-1H-indol-3-yl)acetyl]amino}benzoic acid | 355 | | 3.61 |
| 19 | 3,5-dichloro-2-{[(5-methoxy-2-methyl-1H-indol-3-yl)acetyl]amino}benzoic acid | 407, 409 | | 4.11 |
| 20 | 2-{[(5,6-dimethoxy-2-methyl-1H-indol-3-yl)acetyl]amino}-4-methylbenzoic acid | 383 | | 3.14 |
| 21 | 2-{[(5-chloro-2-methyl-1H-indol-3-yl)acetyl]amino}-4-methylbenzoic acid | 357, 359 | | 3.91 |
| 22 | 2-({[7-(benzyloxy)-1H-indol-3-yl]acetyl}amino)-4-methylbenzoic acid | 415 | | 3.73 |
| 23 | 2-{[(4-chloro-1H-indol-3-yl)acetyl]amino}-4-methylbenzoic acid | 343, 345 | | 3.62 |
| 24 | 2-{[(5,6-dimethoxy-2-methyl-1H-indol-3-yl)acetyl]amino}benzoic acid | 368 | | 2.98 |

EXAMPLE 25

4-[(1E)-3-tert-butoxy-3-oxoprop-1-enyl]-2-{[(5-methoxy-2-methyl-1H-indol-3-yl)acetyl]amino}benzoic acid 3-Bromophthalic anhydride (58.74 g, obtainable from TCl) was dissolved in methanol (200 ml) and refluxed for 24 h. After removal of the methanol in vacuo, the residue was azeotroped with toluene (250 ml). To this residue was added toluene (300 ml), triethylamine (180 ml), diphenylphosphoryl azide (112 ml) and the mixture heated at 80° C. for 1.5 h. Acetone (150 ml) and water (100 ml) were then added and the mixture warmed at 60° C. for 3 h. After dilution with ethyl acetate (1000 ml) the mixture was washed with 1 M aqueous sodium carbonate solution (2×500 ml), brine (250 ml) and dried (MgSO$_4$). Solvent removal in vacuo followed by purification on a 2.5 kg Biotage eluting with 19.2:0.8 petroleum ether: ethyl acetate afforded methyl 4-bromoanthranilate (13.7 g).

5-Methoxy-2-methyl-3-indole acetic acid (5 g, obtainable from Acros), carbonyidiimidazole (4.44 g) and tetrahydrofuran (120 ml) were stirred at room temperature for 30 min after which methyl 4-bromoanthranilate (5.24 g) and pyridinium tosylate (13.69 g) were added and the mixture refluxed for 14 h. After diluting with dichloromethane (200 ml), the residue was washed with 2M hydrochloric acid (200 ml), 2M sodium hydroxide (200 ml), water (200 ml) and brine (200 ml) and dried (MgSO$_4$). After solidifying by treatment with cyclohexane and ethyl acetate, the solid was triturated with ether to afford methyl 4-bromo-2-{[(5-methoxy-2-methyl-1H-indol-3-yl)acetyl]amino}benzoate (6.54 g), MH$^+$ 433, 435; MH$^-$ 431, 433; $T_R$ 3.67 min.

To methyl 4-bromo-2-{[(5-methoxy-2-methyl-1H-indol-3-yl)acetyl]amino}benzoate (20 mg) was added palladium acetate (2 mg), tri-o-tolylphosphine (3 mg), t-butyl acrylate (33 μl), triethylamine (32 μl) and dimethylformamide (1 ml). After heating at 110° C. for 18 h, the solvent was removed in vacuo and the residue diluted with dichloromethane (10 ml) and washed with 5% citric acid (5 ml). Purification by SPE eluting with dichloromethane, chloroform, and chloroform: ether mixtures afforded the title compound (5 mg), MH$^+$ 465; MH$^-$ 463; $T_R$ 4.47 min.

EXAMPLE 26

4-ethyl-2-{[(5-methoxy-2-methyl-1H-indol-3-yl)acetyl]amino}benzoic acid

To methyl 4-bromo-2-{[(5-methoxy-2-methyl-1 H-indol-3-yl)acetyl]amino} benzoate (108 mg) was added tetraethyltin (53 μl) (CAUTION—TOXIC), tetrakis(triphenylphosphine)-palladium (6 mg) and toluene and the mixture refluxed for 6 h. After solvent removal, purification of the faster eluting component by Biotage eluting with 4:1 p40-60 petroleum ether:ethyl acetate afforded a solid (34 mg). To this material was added tetrahydrofuran (5 ml), water (2 ml) and lithium hydroxide (21 mg). After reflux for 18 h, the tetrahydrofuran was removed in vacuo and the product extracted with 3:2 dichloromethane:ethyl acetate. Purification by SPE gave the title compound (25.7 mg) MH$^+$ 367; MH$^-$ 365; $T_R$ 3.70 min.

EXAMPLE 27

2-{[(5-(thiophen-2-yl)-1H-indol-3-yl)acety]amino}-4-methylbenzoic acid

2-{[(5-bromo-1H-indol-3-yl)acetyl]amino}-4-methylbenzoic acid (product of example 6, 48 mg), thiophene-2-boronic acid (17 mg), tetrakis(triphenylphosphine)palladium(0) (12 mg) was heated in a mixture of 2M sodium carbonate solution (0.5 ml) and dimethoxyethane (0.5 ml) for 18 h at 80° C. The mixture was concentrated and diluted with DCM, then washed with 2N HCl for 1 hr. The solvent was reduced and the residue purified by mass-directed automated HPLC to give the title compound (2 mg). MH$^+$391.

The following compounds were prepared in an analogous manner to Example 27:

| Example No. | Compound Name | MH+ |
|---|---|---|
| 28 | 2-{[(5-(2-methoxyphenyl)-1H-indol-3-yl)acetyl]amino}-4-methylbenzoic acid | 415 |
| 29 | 2-{[(5-(3-nitrophenyl)-1H-indol-3-yl)acetyl]amino}-4-methylbenzoic acid | 430 |
| 30 | 2-{[(5-(4-fluorophenyl)-1H-indol-3-yl)acetyl]amino}-4-methylbenzoic acid | 403 |
| 31 | 2-{[(5-(3-methoxyphenyl)-1H-indol-3-yl)acetyl]amino}-4-methylbenzoic acid | 415 |
| 32 | 2-{[(5-(3,4-methylenedioxyphenyl)-1H-indol-3-yl)acetyl]amino}-4-methylbenzoic acid | 429 |
| 33 | 2-{[(5-(3,5-dimethylisoxazol-4-yl)-1H-indol-3-yl)acetyl]amino}-4-methylbenzoic acid | 404 |

BIOLOGICAL DATA

The ability of the compounds to bind to EP4 receptors may be demonstrated in the Human $EP_4$ Scintillation Proximity Assay.

Quantification of radioligand binding by scintillation proximity assay (SPA) is a long-established principle. Briefly, the affinity of compounds for a receptor is assessed by the specific competition between known quantities of radiolabelled ligand compound for that receptor. Increasing concentrations of compound reduce the amount of radiolabel that binds to the receptor. This gives rise to a diminishing scintillation signal from SPA beads coated with membranes that bear the receptor. The signal may be detected with a suitable scintillation counter and the data generated may be analysed with suitable curve-fitting software.

The human $EP_4$ SPA assay (hereafter referred to as 'the assay') utilises membranes prepared from Chinese Hamster Ovary (CHO cells) infected with Semliki Forest Virus (SFV). Genetically engineered SFV-1 viral particles containing the genetic sequence of the human EP4 receptor were used to infect CHO cells resulting in expression of th receptor protein in cellular membranes.

Cells washed free of media are homogenised in a pH-buffered medium containing peptidase inhibitors. A suitable buffer is of the following composition: 50 mM HEPES, 1 mM EDTA, 25 µg/ml bacitracin, 100 µM leupeptin, 1 mM PMSF, 2 µM Pepstatin A, pH adjusted to 7.4 with KOH. Following removal of cell debris by a low-speed centrifugation, a pellet of membranes is prepared by a high-speed (48000 g) centrifugation of the resulting supernatant. Membrane suspensions such as that described may be stored at −80° C. until used.

For assay, membranes expressing human $EP_4$ receptors are diluted in a pH-buffered medium and mixed with SPA beads coated with a suitable substance to facilitate the adhesion of membranes to the beads. The concentrations of membrane protein and SPA beads chosen should result in SPA binding signal of at least 300 corrected counts per minute (CCPM) when tritiated radioligand at a concentration close to its $K_d$ (affinity value) is combined with the mixture. Non-specific binding (nsb) may be determined by competition between the radiolabelled ligand and a saturating concentration of unlabelled ligand. In order to quantify the affinity of EP4 receptor ligands, compounds are diluted in a stepwise manner across the wells of a 96-well plate. Radioligand, compound, and unlabelled ligand are then added to a 96-well plate suitable for the measurement of SPA binding signals prior to the addition of bead/membrane mixture to initiate the binding reaction. Equilibrium may be achieved by incubation at room temperature for 120 minutes prior to scintillation counting. The data so generated may be analysed by means of a computerised curve-fitting routine in order to quantify the concentration of compound that displaces 50% of the specific radioligand binding ($IC_{50}$). The affinity ($pK_i$) of the compound may be calculated from the $IC_{50}$ by application of the Cheng-Prusoff correction. Suitable reagents and protocols are: reaction buffer containing 50 mM HEPES, 10 mM $MgCl_2$, pH adjusted to 7.4 with KOH; SPA beads coated with wheatgerm agglutinin; 1.25 nM [$^3$H]-prostaglandin $E_2$ as radioligand; 10 µM prostaglandin $E_2$ as unlabelled ligand; a three-fold dilution series of compound starting at 10 µM and ending at 0.3 nM is adequate.

The ability of the compounds to antagonise EP4 receptors may b demonstrated in the [$^{125}$I]cAMP Scintillation Proximity Assay (hereafter referred to as 'the cAMP assay'). The cAMP assay utilises HEK-293 cells expressing the recombinant human EP4 receptor, obtained from Receptor Biology, Inc. Beltsville, Md., USA. The cells were cultured in Dulbecco's Modified Eagle Medium—HAM F12 mix (DMEM-F12), containing 10% heat inactivated-foetal bovine serum (FBS) and 2 mM L-glutamine. The cells were either passaged into fresh medium or used in an assay once 90% confluency as determined visually had been achieved.

The cells were harvested by treatment with Versene, re-suspended in fresh culture medium and plated out to yield approximately 10,000 cells per well of a 96-well plate for overnight culture in culture medium additionally supplemented with 3 µM indomethacin. For assay, the culture medium was replaced with assay medium (DMEM-F12 containing 300 µM isobutylmethylxanthine (IBMX) and 3 µM indomethacin) and incubated for 30 minutes. Following this, antagonist was then added at various concentrations such that an entire agonist concentration-effect curve could be obtained in the presence of a single concentration of the antagonist. The antagonist was allowed to equilibrate with the cells for 30 minutes. Subsequently the cells were challenged with an agonist for 15 minutes. The reaction was stopped by the aspiration of the assay medium and the addition of ice-cold ethanol. All incubations were carried out at 37C. in a 5% carbon dioxide atmosphere. Care was taken to ensure the constancy of IBMX, indomethacin and vehicle (DMSO) concentrations throughout. The amount of cAMP in each well was then determined by [$^{125}$I]cAMP scintillation proximity assay using a proprietary kit, obtained from Amersham, Buckinghamshire, UK, and according to the manufacturer's instructions.

Data from cAMP assays were expressed as pmol cAMP per well. A four-parameter logistic equation of the form:

$$E=((Em.[A]^{\wedge}nH)/((EC_{50}^{\wedge}nH)+([A]^{\wedge}nH))$$

was then fitted to E/[A] curve data in order to estimate maximum effect (Em), curve mid-point (EC50), and Hill slope (nH); other terms in the equation are effect (E) and concentration ([A]). Individual estimates of curve parameters were obtained from each curve. An empirical estimate of antagonist affinity ($pA_2$) could then be obtained using the following formula:

$$pA_2=\log((EC_{50}^B/EC_{50}^A)-1)-\log[B]$$

where $EC_{50}^A$ is the midpoint of a control agonist concentration-effect curve in the absence of antagonist; $EC_{50}^B$ is th midpoint of an agonist concentration effect curve produced in the presence of a fixed concentration of antagonist; and [B] is the concentration of antagonist used. Estimates from individual experiments were then averaged to provide mean data. Quoted values are therefore the mean±standard deviation (s.d.) of n separate experiments, each derived from a separate cAMP assay.

For the rigorous estimation of antagonist affinity values ($pK_b$) the method of Arunlakshana and Schild was employed. Briefly, the midpoint of agonist concentration/effect curves in the presence and absence of antagonist are used to calculate concentration ratios (CR). Linear regression is performed on a plot of (CR-1) against concentration of antagonist (–log[B]) in order to estimate the point of intersection with the concentration (–log[B]) axis and the slope of the line. If the slope of the regression does not differ significantly from unity then it may be constrained to 1.0. Under this latter circumstance, the point of intersection on the concentration axis represents the affinity ($pK_b$) of the antagonist.

All of the compounds exemplified have a $pK_i$ of 6.0 or greater at EP4 receptors as determined using the above-mentioned procedure:

The compounds synthesised in examples 1, 2, 3, 4, 6, 7, 9, 10, 11, 12, 13, 17, 20, 21 and 26 have a $pK_i$ of 7.0 or greater at EP4 receptors as determined using the above-mentioned procedure.

The compound synthesised in example 1 has a $pK_b$ greater than 8.0 at EP4 receptors as determined using the above-mentioned procedure.

What is claimed is:

1. A compounds of formula (I):

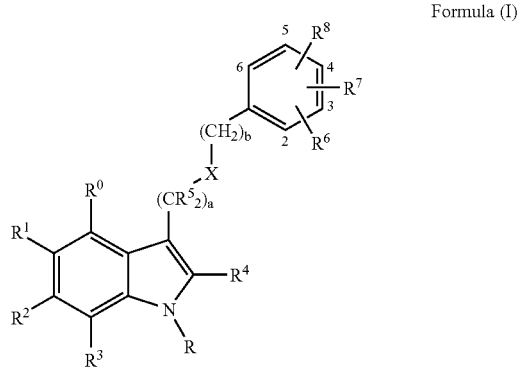

Formula (I)

or salts or solvates thereof or physiologically functional derivatives thereof wherein:
a=0, 1 or 2;
b=0 or 1;
X is selected from the group consisting of C(O)NR;
R is selected from the group consisting of H and $C_{1-4}$ alkyl;
$R^0$, $R^1$, $R^2$ and $R^3$ each independently are selected from the group consisting of H, halogen, $C_{1-6}$alkyl, S—$C_{1-6}$alkyl, $C_{1-6}$alkoxy, $OCF_3$, $OCH_2CF_3$, O-cyclopropyl, $OCH_2$-cyclopropyl, $NH_2$, $NHC_{1-6}$alkyl, $N(C_{1-6}$alkyl$)_2$, $NO_2$, OH, $CH_2OC_{1-6}$alkyl, $CH_2OH$, aryl$C_{1-6}$alkylenoxy, $C_{1-6}$alkyl-$SO_2NH$—$C_{1-4}$alkylene, aryl and heteroaryl;
$R^4$ is selected from the group consisting of H, $C_{1-6}$alkyl, aryl and heteroaryl;
$R^5$ each is independently selected from the group consisting of H, $CH_3$ and F;
$R^6$ is selected from the group consisting of $SO_3H$, $SO_2NH_2$, $CH_2CO_2H$, $SO_2NHCOR$, $CONHSO_2R$, $P(O)(OH)_2$, heteroaryl and C(O)Z where Z is OH or $NR^9_2$ wherein each $R^9$ independently is selected from the group consisting of H, $C_{1-6}$alkyl and $SO_2(CH_2)_c$aryl, wherein c=0 or 1;

$R^7$ is selected from the group consisting of H, $C_{1-6}$alkyl, $C_{1-6}$alkoxy, halogen, $NO_2$, CH=$CHCO_2C_{1-6}$alkyl, $NHCOC_{1-6}$alkyl, $C_{1-2}$perfluoroalkyl, OH and $CO_2R^{10}$ wherein $R^{10}$ is selected from the group consisting of H and $C_{1-6}$alkyl; and $R^8$ is H, or $R^8$ is selected from the group consisting of $C_{1-6}$alkyl, $C_{1-6}$alkoxy and halogen, when $R^7$ is selected from the group consisting of $C_{1-6}$alkyl, $C_{1-6}$alkoxy and halogen; or $R^7$, $R^8$ and the benzene ring to which they are attached are taken together to form a naphthyl group or a benzene ring fused to a heteroaryl group; or $R^7$ and $R^8$ are taken together to form a vicinal $OC(CH_3)_2O$ group; and provided that:
when $R^6$ is C(O)Z, wherein Z is OH, X is C(O)NR and $R^0$, R, $R^1$, $R^2$, $R^3$, $R^4$, $R^5$, $R^7$ and $R^8$=H and a=0, 1 or 2, then b=1.

2. A process for preparation of a compound of formula (I) or a salt or solvate thereof or a physiologically functional derivative thereof as claimed in claim 1, said process comprising:

(A) coupling an acid of formula (II):

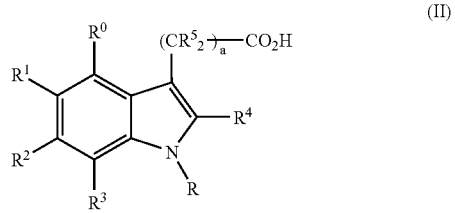

or a protected derivative thereof, with an amine of formula (III):

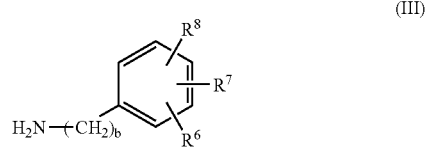

or a protected derivative thereof; or (B) coupling an acid of formula (V):

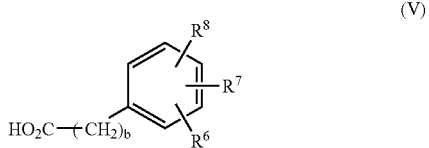

or a protected derivative thereof, with an amine of formula (IV):

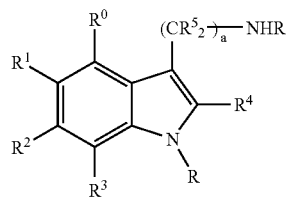

or a protected derivative thereof; or
(C) interconverting a compound of formula (I) into another compound of formula (I); or
(D) deprotecting a protected derivative of compound of formula (I); and optionally converting compounds of formula (I) prepared by any one of processes or process steps (A) to (D) into a salt or solvate thereof or a physiologically functional derivative thereof.

3. A pharmaceutical composition, comprising a compound of formula (I) or a salt or solvate thereof or a physiologically functional derivative thereof as claimed in claim 1 in admixture with one or more physiologically acceptable carriers or excipients.

4. A method for treating inflammatory pain in a human or animal subject, which comprises administering to the subject an effective amount of a compound of formula (I), a salt, solvate, or a physiologically functional derivative thereof of claim 1.

5. A compound which is selected from:
2-{[(5-methoxy-2-methyl-1H-indol-3-yl)acetyl]amino}-4-methylbenzoic acid (Example 1);
2-[(1H-indol-3-ylacetyl)amino]-4-methylbenzoic acid (Example 2);
4-methyl-2-{[(2-methyl-1H-indol-3-yl)acetyl]amino}benzoic acid (Example 3);
2-{[(5-fluoro-1H-indol-3-yl)acetyl]amino}-4-methylbenzoic acid (Example 4);
2-({[5-(benzyloxy)-1H-indol-3-yl]acetyl}amino)-4-methylbenzoic acid (Example 5);
2-{[(5-bromo-1H-indol-3-yl)acetyl]amino}-4-methylbenzoic acid (Example 6);
2-{[(5-methoxy-1H-indol-3-yl)acetyl]amino}-4-methylbenzoic acid (Example 7);
4-bromo-2-{[(5-methoxy-2-methyl-1H-indol-3-yl)acetyl]amino}benzoic acid (Example 8);
4-methyl-2-{[(2-phenyl-1H-indol-3-yl)acetyl]amino}benzoic acid (Example 9);
4-fluoro-2-{[(5-methoxy-2-methyl-1H-indol-3-yl)acetyl]amino}benzoic acid (Example 10);
4-chloro-2-{[(5-methoxy-2-methyl-1H-indol-3-yl)acetyl]amino}benzoic acid (Example 11);
2-{[(5-methoxy-2-methyl-1H-indol-3-yl)acetyl]amino}-4-nitrobenzoic acid (Example 12);
2-{[(5-methoxy-2-methyl-1H-indol-3-yl)acetyl]amino}benzoic acid (Example 13);
5-chloro-2-{[(5-methoxy-2-methyl-1H-indol-3-yl)acetyl]amino}benzoic acid (Example 14);
4,5-difluoro-2-{[(5-methoxy-2-methyl-1H-indol-3-yl)acetyl]amino}benzoic acid (Example 15);
2-{[(5-methoxy-2-methyl-1H-indol-3-yl)acetyl]amino}-5-methylbenzoic acid (Example 16);
2-{[(5-methoxy-2-methyl-1H-indol-3-yl)acetyl]amino}-4-(trifluoromethyl)benzoic acid (Example 17);
3-hydroxy-2-{[(5-methoxy-2-methyl-1H-indol-3-yl)acetyl]amino}benzoic acid (Example 18);
3,5-dichloro-2-{[(5-methoxy-2-methyl-1H-indol-3-yl)acetyl]amino}benzoic acid (Example 19);
2-{[(5,6-dimethoxy-2-methyl-1H-indol-3-yl)acetyl]amino}-4-methylbenzoic acid (Example 20);
2-{[(5-chloro-2-methyl-1H-indol-3-yl)acetyl]amino}-4-methylbenzoic acid (Example 21);
2-({[7-(benzyloxy)-1H-indol-3-yl]acetyl}amino)-4-methylbenzoic acid (Example 22);
2-{[(4-chloro-1H-indol-3-yl)acetyl]amino}-4-methylbenzoic acid (Example 23);
2-{[(5,6-dimethoxy-2-methyl-1H-indol-3-yl)acetyl]amino}benzoic acid (Example 24);
4-[(1E)-3-tert-butoxy-3-oxoprop-1-enyl]-2-{[(5-methoxy-2-methyl-1H-indol-3-yl)acetyl]amino}benzoic acid (Example 25);
4-ethyl-2-{[(5-methoxy-2-methyl-1H-indol-3-yl)acetyl]amino}benzoic acid (Example 26);
2-{[(5-(2-methoxyphenyl)-1H-indol-3-yl)acetyl]amino}-4-methylbenzoic acid (Example 28);
2-{[(5-(3-nitrophenyl)-1H-indol-3-yl)acetyl]amino}-4-methylbenzoic acid (Example 29);
2-{[(5-(4-fluorophenyl)-1H-indol-3-yl)acetyl]amino}-4-methylbenzoic acid (Example 30); or
2-{[(5-(3-methoxyphenyl)-1H-indol-3-yl)acetyl]amino}-4-methylbenzoic acid (Example 31).

6. A compound according to claim 5 which is:
2-{[(5-methoxy-2-methyl-1H-indol-3-yl)acetyl]amino}-4-methylbenzoic acid (Example 1).

7. A compound according to claim 5 which is:
2-{[(5-methoxy-2-methyl-1H-indol-3-yl)acetyl]amino}benzoic acid (Example 13).

8. A compound according to claim 5 which is selected from:
2-[(1H-indol-3-ylacetyl)amino]-4-methylbenzoic acid (Example 2);
4-methyl-2-{[(2-methyl-1H-indol-3-yl)acetyl]amino}benzoic acid (Example 3);
2-{[(5-fluoro-1H-indol-3-yl)acetyl]amino}-4-methylbenzoic acid (Example 4);
2-{[(5-methoxy-1H-indol-3-yl)acetyl]amino}-4-methylbenzoic acid (Example 7);
2-{[(5-chloro-2-methyl-1H-indol-3-yl)acetyl]amino}-4-methlybenzoic acid (Example 21); or
4-ethyl-2-{[(5-methoxy-2-methyl-1H-indol-3-yl)acetyl]amino}benzoic acid (Example 26).

* * * * *